US008486545B2

(12) United States Patent
Lanning et al.

(10) Patent No.: US 8,486,545 B2
(45) Date of Patent: Jul. 16, 2013

(54) SYSTEMS AND METHODS FOR FLAW DETECTION AND MONITORING AT ELEVATED TEMPERATURES WITH WIRELESS COMMUNICATION USING SURFACE EMBEDDED, MONOLITHICALLY INTEGRATED, THIN-FILM, MAGNETICALLY ACTUATED SENSORS, AND METHODS FOR FABRICATING THE SENSORS

(75) Inventors: Bruce R. Lanning, Littleton, CO (US); Glenn M. Light, San Antonio, TX (US); Stephen J. Hudak, Jr., Helotes, TX (US); James A. Moryl, Helotes, TX (US)

(73) Assignee: Southwest Research Institute, San Antonio, TX (US)

( * ) Notice: Subject to any disclaimer, the term of this patent is extended or adjusted under 35 U.S.C. 154(b) by 591 days.

(21) Appl. No.: 11/540,495

(22) Filed: Sep. 28, 2006

(65) Prior Publication Data
US 2007/0108973 A1 May 17, 2007

Related U.S. Application Data

(60) Provisional application No. 60/721,922, filed on Sep. 28, 2005.

(51) Int. Cl.
*G01N 29/04* (2006.01)
*G01R 33/18* (2006.01)
*H01L 41/06* (2006.01)

(52) U.S. Cl.
CPC ..................................... *H01L 41/06* (2013.01)
USPC ........ 428/692.1; 324/237; 324/238; 324/240; 324/241; 324/242; 73/598

(58) Field of Classification Search
None
See application file for complete search history.

(56) References Cited

U.S. PATENT DOCUMENTS

| 4,139,822 | A | 2/1979 | Urich et al. |
| 4,685,335 | A | 8/1987 | Sato et al. |
| 4,741,203 | A | 5/1988 | Willaman et al. |
| 4,750,072 | A | 6/1988 | Takagi |
| 4,955,269 | A | 9/1990 | Kendig et al. |
| 5,140,264 | A | 8/1992 | Metala et al. |

(Continued)

OTHER PUBLICATIONS

Ludwig et al. "Giant magnetostrictive thin films for applications in microelectromechanical systems", J. Applied Physics, 87(9):4691-4695, 2000.*

(Continued)

*Primary Examiner* — Kevin Bernatz
(74) *Attorney, Agent, or Firm* — Kammer Browning PLLC

(57) ABSTRACT

Systems and methods for flaw detection and monitoring at elevated temperatures with wireless communication using surface embedded, monolithically integrated, thin-film, magnetically actuated sensors, and methods for fabricating the sensors. The sensor is a monolithically integrated, multi-layered (nano-composite), thin-film sensor structure that incorporates a thin-film, multi-layer magnetostrictive element, a thin-film electrically insulating or dielectric layer, and a thin-film activating layer such as a planar coil. The method for manufacturing the multi-layered, thin-film sensor structure as described above, utilizes a variety of factors that allow for optimization of sensor characteristics for application to specific structures and in specific environments. The system and method integrating the multi-layered, thin-film sensor structure as described above, further utilizes wireless connectivity to the sensor to allow the sensor to be mounted on moving components within the monitored assembly.

13 Claims, 12 Drawing Sheets

U.S. PATENT DOCUMENTS

| | | | |
|---|---|---|---|
| 5,260,615 A | | 11/1993 | Sahashi et al. |
| 5,450,755 A | * | 9/1995 | Saito et al. ................ 73/763 |
| 5,663,504 A | | 9/1997 | Kluft |
| 5,670,879 A | | 9/1997 | Zombo et al. |
| 5,811,682 A | * | 9/1998 | Ohtani et al. ................ 73/643 |
| 5,959,388 A | | 9/1999 | Graebner et al. |
| 6,038,925 A | * | 3/2000 | Ohtani et al. ................ 73/598 |
| 6,109,108 A | * | 8/2000 | Ohtani et al. ................ 73/599 |
| 6,122,150 A | | 9/2000 | Gill |
| 6,168,860 B1 | | 1/2001 | Daughton |
| 6,362,543 B1 | | 3/2002 | Ellis |
| 6,384,600 B1 | * | 5/2002 | Coehoorn ................ 324/252 |
| 6,424,150 B2 | * | 7/2002 | Kwun et al. ................ 324/216 |
| 6,556,007 B1 | * | 4/2003 | Abe et al. ................ 324/252 |
| 6,579,612 B1 | | 6/2003 | Lille |
| 6,639,402 B2 | * | 10/2003 | Grimes et al. ................ 324/239 |
| 6,873,545 B2 | | 3/2005 | Johnson |
| 6,917,196 B2 | * | 7/2005 | Kwun et al. ................ 324/240 |
| 6,943,570 B2 | | 9/2005 | Duffy et al. |
| 7,077,010 B2 | * | 7/2006 | Ganapathi ................ 73/779 |
| 7,498,805 B2 | * | 3/2009 | Siegle et al. ................ 324/252 |
| 7,583,081 B2 | * | 9/2009 | Schmitt et al. ................ 324/252 |
| 8,274,282 B2 | * | 9/2012 | Decitre et al. ................ 324/262 |
| 2002/0105324 A1 | * | 8/2002 | Kwun et al. ................ 324/240 |
| 2004/0050172 A1 | * | 3/2004 | Quandt et al. ................ 73/779 |
| 2004/0095137 A1 | * | 5/2004 | Kwun et al. ................ 324/240 |
| 2007/0229066 A1 | * | 10/2007 | Narishige et al. ................ 324/222 |
| 2009/0206831 A1 | * | 8/2009 | Fermon et al. ................ 324/240 |

OTHER PUBLICATIONS

Quandt et al. "Mangetic properties and microstructure of giant magnetostrictive TbFe/FeCo multilayers", J. Applied Physics, 83(11):7267-7269, 1998.*

* cited by examiner

SYSTEMS AND METHODS FOR FLAW DETECTION AND MONITORING AT ELEVATED TEMPERATURES WITH WIRELESS COMMUNICATION USING SURFACE EMBEDDED, MONOLITHICALLY INTEGRATED, THIN-FILM, MAGNETICALLY ACTUATED SENSORS, AND METHODS FOR FABRICATING THE SENSORS

CROSS REFERENCE TO RELATED APPLICATIONS

This application claims the benefit under Title 35 United States Code §119(e) of U.S. Provisional Application No. 60/721,922 filed Sep. 28, 2005, the full disclosure of which is incorporated herein by reference.

BACKGROUND OF THE INVENTION

1. Field of the Invention

The present invention relates generally to systems and methods for flaw detection in physical structures, especially high value asset structures. The present invention relates more specifically to systems and methods for flaw detection and monitoring at elevated temperatures with wireless communication using surface embedded, monolithically integrated, thin-film, magnetically actuated sensors, and additionally to methods for fabricating sensors used in such systems.

2. Description of the Related Art

High quality, robust sensors capable of on-board detection and monitoring of damage would result in significant enhancements to the safety, reliability, and availability of high value assets, while minimizing their total life cycle costs. For highly stressed, fatigue-critical components, such as rotating components in turbines and rotorcraft, one would ideally like to obtain a direct measure of the state of damage in the material. However, obtaining such a measurement presents numerous technical challenges arising from the thermal and stress environments, combined with the high rotational speed and limited accessibility of such systems. Consequently, it is not surprising that there are presently no operational sensors for direct measurement of material damage (cracking) during component operation.

Attempts have also been made to use acoustic emission (AE) sensors to extract cracking signatures from the numerous sources of acoustic activity that accompany component operation. Although vibration and AE measurements are relatively easy to make, analyzing the results in order to extract the cracking signature from the overall rotor dynamics, or the acoustic background, continues to be a significant challenge.

A variety of nondestructive evaluation (NDE) techniques have been developed and refined for measurement of cracks to relatively small sizes (0.020 in.-0.030 in.) in depot based inspections. However, these techniques require component disassembly and a relatively well controlled environment; consequently they are not adaptable to on-line sensing in the operating environment. The development paradigm for such depot NDE techniques is very different from that needed to develop functional on-board sensors. Traditional depot-type inspections are driven by economics, which dictate that they be done relatively infrequently, and thus with high sensitivity, to ensure that damage (cracks) are small so that the component can survive until the next inspection, which is often ten years or more in the future.

The science and technology of prognosis and structural health management offer the potential for significant enhancements in the safety, reliability and readiness of high-value assets. For the case of turbine engines, this concept is based on a closed-loop process whose successful implementation depends on the integration of several multidisciplinary elements including: 1) onboard sensing of operational parameters and material damage states; 2) diagnosing trends, fault conditions, and underlying damage; 3) prognosing (predicting) remaining useful life in terms of probability of failure and limits on reliable performance, and 4) deciding upon appropriate courses of action. For example, whether or not the asset is capable of performing a given mission, or alternatively, is in need of inspection, maintenance, or replacement. As indicated, a wide variety of hardware and software tools are needed to facilitate these process steps. However, considerable uncertainty exists in the usage and sensor inputs, as well as the required modeling and associated materials property inputs. Consequently, there is an inherent need for the reasoning element of the prognosis system to be probabilistically-based.

Complementing the variety of onboard sensors are traditional health monitoring software tools for pattern recognition, neural networks, Bayesian updating, expert systems, and fuzzy logic. The advantage of these tools is that, when properly applied, they are highly efficient and thus amenable to onboard monitoring and real-time data interpretation. However, the disadvantage of these tools is that they rarely involve consideration of the underlying physical processes. Consequently, they require considerable empirical calibration or "training" for each specific application of interest. In contrast, probabilistic life prediction is typically based on materials property data, finite element thermal and stress analysis, pre-service inspection and in-service monitoring for defects, and damage accumulation algorithms. The advantage of this approach is that it is more amenable to linkage with the underlying physical mechanisms of damage (i.e., crack nucleation and growth). Thus, the process is inherently suitable for extension into materials prognosis, a concept that combines information on the material damage state with mechanistically-based predictive models.

The fundamental goal of all of these approaches is to facilitate better-informed decisions, whether for mission planning in the field (over the short term), or sustainment at the depot (over the longer term). In fact, the optimum prognosis system is likely to be some combination of traditional data-driven methods and probabilistic mechanics methods. Thus, in many respects the above tools can be viewed as being complementary.

With regard to on-board crack detection in fatigue-critical components, the important question becomes: What detection sensitivity is sufficient to provide the desired component reliability, provided essentially continuous inspections can be conducted, either during or after each operation cycle? Studies have been carried out involving, for example, probabilistic simulation of low-cycle fatigue crack initiation and growth at a bolt hole of a typical compressor disc in a military turbine engine. Predicted probabilities of failure over the life of the disc have been evaluated for various inspection scenarios ranging from no inspections to continual inspections with varying sensitivities. The probability of failure under such conditions begins to increase first for the case where no inspection is performed. In contrast, inspections performed continually (i.e. once every flight) result in markedly lower probability of failure even with relatively coarse inspection sensitivities of 200 to 300 mils (in size). For these cases, acceptable probabilities of failure are maintained by inspecting on each flight and removing defective discs from service. The results obtained under these studies show that sensitivities of 200 to 300 mils can be effective for on-board monitoring for cases where critical crack sizes exceed these values. Continual monitoring with sensitivities 10 times lower than those typically employed in depot inspections (20-30 mils) are effective because of the trade-off between inspection sensitivity and inspection frequency. In other words, on-board inspections do not require high sensitivity to be effective because they only need to find cracks that will not grow to failure in the next few flights. Similar benefits of continual on-board monitoring are anticipated for fatigue critical components, although specific results will obviously depend on the critical crack size in the component, and thus will be component dependent.

It would therefore be desirable to have a system (and a method of operating the system) that is capable of on-board detection and monitoring of cracks in critical structures with a sensitivity that is commensurate with the frequency of interrogation made possible by the system. It would be desirable for such a system to utilize a sensor structure that is robust enough to withstand the vibrational and thermal extremes typically experienced within such high-value asset systems (such as turbines and rotors). It would therefore be desirable to include wireless connectivity to and from the sensor structure(s) that could operate within the high level EM noise environment of rotating metal components. It would further be desirable to provide a versatile sensor manufacturing process that could create customized sensors suitable for specific structural systems and specific operating environments.

SUMMARY OF THE INVENTION

One embodiment (that forms the basis of the present invention) for using embedded sensors in association with a system for monitoring a turbine engine disc is illustrated in FIG. 1. The system as generally shown includes a plurality of sensors 30 (as described in greater detail below) that are placed (for example) near fracture critical components such as turbine blades 22 and turbine discs 24. These sensors 30 positioned on the moving components 12 of turbine engine 10 are in wireless RF signal connection to a receiving antenna 14 positioned on a stationary component of engine 10. Antenna 14 is connected through a signal line 16 to data processing instrumentation 20 for signal analysis. This concept includes distributed thin-film magnetostrictive sensors that are integrated onto the component surface near fracture critical locations (FCLs). Periodically activating the thin-film sensors by generating ultrasonic waves enables interrogation of the material component for defects through the detection of reflected waves from the defect using the "pulse-echo" mode of detection. The complete sensor system concept also includes a fully integrated antenna for the harvesting of energy using microwaves (or other frequency electromagnetic waves) thereby providing power for sensor activation and radio frequency (RF) communication of the backscattered ultrasonic signals. This fully integrated, monolithic, wireless, self-powered crack detection sensor provides effective structural health management and prognosis in turbine engines, as well as other high-value assets.

A thin-film sensor form factor offers unique advantages over other detector architectures in terms of performance and integration simplicity (a relatively simple architecture for monolithic surface integration), mass-production compatibility to micro-system manufacturing processes, and durability under the severe challenges posed by high-temperature operating environments. In theory, several thin-film materials and associated physical phenomenon are possible including magnetostrictive (Ms), piezoelectric, or shape memory, all of which can be deposited as thin films. However, magnetostrictive thin films are seen as providing one of the best modes for structuring a sensor for use in the system of the present invention since they offer several attractive features: a) a high energy output for remote-control actuation and communication, b) a wide range of candidate material systems (and associated process flexibility to meet end-use requirements), and c) inherent durability and robustness.

Significant enhancements in the reliability and readiness of high-value assets are achievable by implementing prognosis systems such as described by the present invention. This real time, or near-real time, decision making process is based on the acquisition and fusion of on-line sensor feedback, combined with physics-based analytical models for damage accumulation, and higher order reasoning for decision making.

The present invention therefore provides: (1) a monolithically integrated, multi-layered (nano-composite), thin-film sensor structure that incorporates a thin-film, multi-layer magnetostrictive element, a thin-film electrically insulating or dielectric layer, and a thin-film activating layer such as a planar coil; (2) a method for manufacturing the multi-layered, thin-film sensor structure as described above, utilizing a variety of factors that allow for optimization of sensor characteristics for application to specific structures and in specific environments; (3) a system and a method integrating the multi-layered, thin-film sensor structure as described above, and further utilizing wireless connectivity to the sensor mounted on moving components within the monitored assembly.

The method for manufacturing the engineered, monolithically integrated, multi-layered (nano-composite), thin-film structure includes a number of customizing factors including the magnetron sputtering (or vapor deposition) of alternating layers of a high (hard) magnetostrictive material (iron/rare earth or similar alloy) and a high magnetization (soft) material (FeCo or similar) directly onto sensing platform or onto a flexible backing substrate that can later be affixed to sensing platform. Composite magnetostrictive layer properties, such as magnetostriction coefficient, saturation magnetization, and Curie temperature (thermal stability), can be engineered by adjusting layer thicknesses (2 nm-50 nm), soft/hard layer ratio (typically greater than 1) and sputtering deposition parameters (with and without ion assist and/or RF sample bias) with minimum total layered composite thickness such that losses due to skin depth effects are minimized (typically greater than 3 microns). Composite magnetostrictive layers can also be post-annealed in a magnetic bias field or annealed in-situ as part of elevated temperature service to enhance performance.

The dielectric layer may be composed of a number of different materials, such as oxides, nitrides, carbides, or others, to be deposited over top of the composite layer using reactive magnetron sputtering (or other compatible methods) to serve as an electrically insulating layer and for resistance to high temperature oxidizing environments, again with thicknesses generally not to exceed 3 microns.

The activation layer may preferably comprise a conductive planar antenna coil, to be deposited through shadow mask techniques directly on top of the dielectric layer.

In addition, the method of manufacturing may include steps in which the surface of the sensing platform is treated chemically, thermally, or mechanically (or coated with an adhesion promoter layer) to optimize impedance and mechanical adhesion of the composite magnetostrictive film at elevated temperatures. As a result, the monolithically integrated sensor may be applied to different types of sensing platforms (other engineering metals, composites, etc.) or applied to flexible (or thin) film supports which are then bonded to the engineering platform.

A further important aspect of the manufacturing process may include steps in which the magnetic spin orientation is engineered, thereby eliminating the need for magnetic biasing with permanent magnets prior to activation, or during operation. The manufacturing method may also include steps in which the dielectric layer and activation layer are deposited by methods other than magnetron sputtering, such as other PVD, wet chemical, or plasma/flame spray techniques. Other types of magnetostrictive materials (other than iron-based) may also be substituted to achieve specific properties or enhance actuation performance.

The monolithically integrated sensor manufactured as described above may further be utilized for applications other than flaw detection, such as temperature, strain, and other structural/material phenomena measurable through signal modification. The thin-film sensor, consisting of multiple layers, that is magnetostrictive when used with an RF excitation, can produce ultrasonic waves (guided as well as bulk) in the monitored material and can operate at temperatures as high as 1200° F.

The methods of employing wireless communication techniques allow the system to transmit the data acquired by the thin-film multi-layer sensor to a receiver antenna near or within the component under interrogation. These methods include passive wireless communication of a response signal from the magnetostrictive sensor. The wireless connectivity design of the system may further include an RF backscatter modulator circuit with high fidelity for communicating analog response signals from the magnetostrictive sensor. Finally, the wireless connectivity feature of the system of the present invention may include the coupling of RF signals from an antenna on a stationary component of the assembly being investigated, to an RF backscatter modulator on the rotating component of the assembly.

Variations on the above described systems, sensors, and methods that fall within the scope of the present invention will become apparent to those skilled in the art from the following descriptions and disclosures.

DETAILED DESCRIPTION OF THE PREFERRED EMBODIMENTS

Probabilistic Analysis of Prognosis Uncertainty (Preliminary Discussion)

Figure 1:
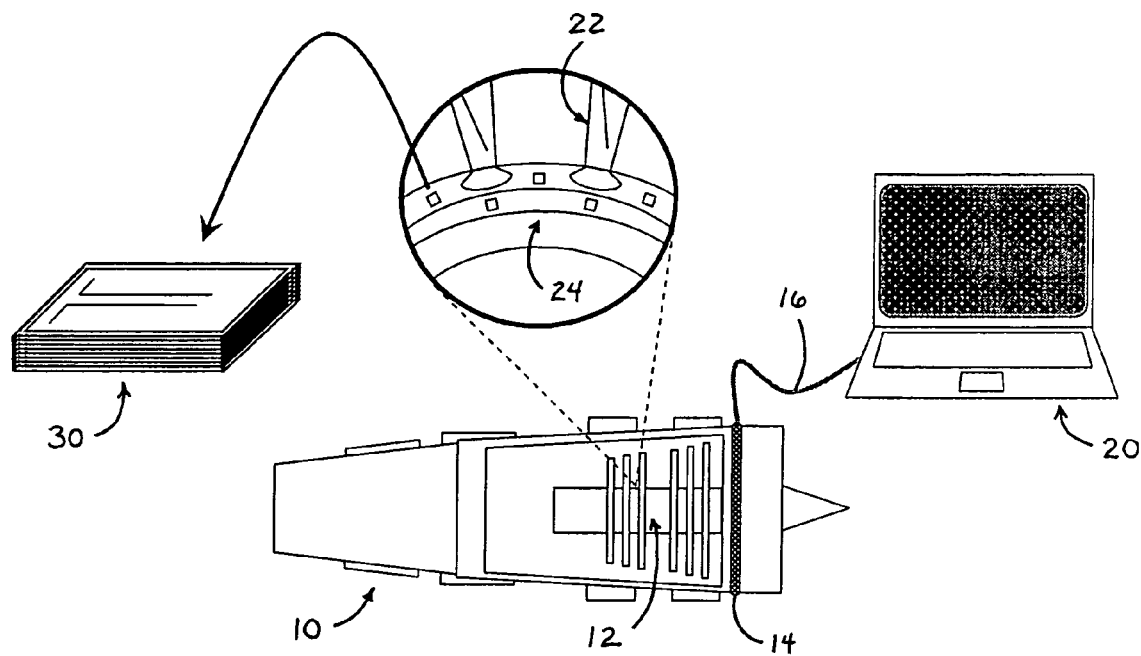
FIG. 1 is a functional schematic diagram of the wireless thin-film magnetostrictive sensing approach implemented by the systems and methods of the present invention.
Figure 2:
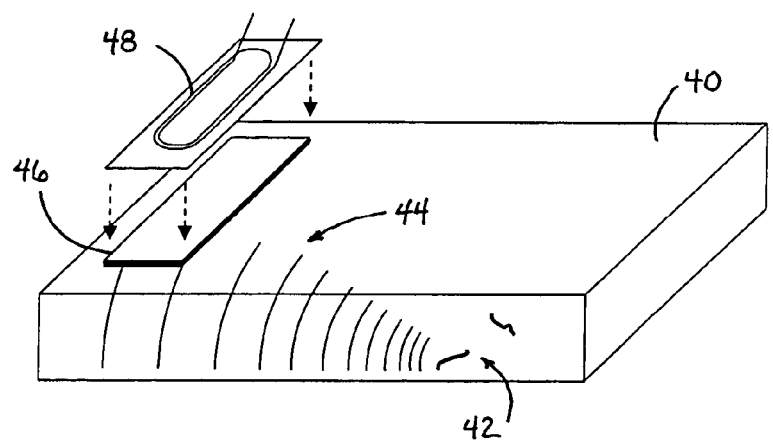
FIG. 2 is a schematic perspective view of a basic system for carrying out the magnetostrictive sensing of material defects.

Probabilistic analyses (detailed in the above referenced Provisional Patent Application, the disclosure of which has been incorporated herein by reference) suggests that continual monitoring of with sensors that are 6 to 10 times less sensitive than those presently used in depot inspections (about 30 mils) can achieve high component reliability (low probabilities of failure). This benefit results from the continual feedback that enables damaged components to be identified and removed from service throughout their life. Although this concept of trading-off interrogation sensitivity for frequency of interrogation is believed to be generally true, the specific minimum sensitivities required for effective onboard sensing will depend on the critical crack size associated with the specific fatigue critical location. That is, for the specific case of a bolt-hole in a generic disc, for example, the critical crack size may be greater than 300 mils; thus sensors with 200 mil to 300 mil sensitivity would be able to detect and signal the removal of cracks before they became critical. However, in general there may exist fatigue critical locations in fracture-critical components that have critical crack sizes less than 300 mils, in which case the onboard sensor would need to have greater sensitivity than 300 mils. The Overall System: Multi-Layer Thin-Film Sensor with Induction Coil, Wireless Sensor Excitation/Activation, Wireless Sensor Signal Transmission, Remote Receiver & Signal Processor The basic physics by which magnetostrictive sensing occurs is schematically illustrated in FIG. 2. Four basic components are required: 1) an induction coil 48 for transduction of an electric current into a magnetic flux, 2) a ferromagnetic strip 46 for transduction of the magnetic flux into a displacement based on the magnetostrictive effect, 3) a fixed magnetic field to enhance the efficiency of energy transduction process (not shown), and 4) associated power amplification and signal conditioning (not shown). In this manner, fatigue cracks 42 in a material structure 40 under investigation, may be detected by means of sensing the return elastic waves with the magnetostrictive sensor (combination of 46 & 48).

To effectively detect surface and sub-surface fatigue damage non-destructively, a sensor must be in intimate contact with the material surface, and therefore able to withstand the harsh thermal and stress environment that exists within the engine. Thin-film sensor architecture, with negligible mass, provides a minimally intrusive means of measuring surface/bulk parameters as it can be vacuum-deposited directly onto the surface. Fatigue cracking would be monitored via injection and scattering of elastic waves from defects and results would be communicated wirelessly to overcome the inaccessibility problem.

Injection and corresponding detection of scattered elastic waves is accomplished through the conversion of electrical to mechanical and mechanical to electrical energies. For the current sensor concept, these changes could theoretically be transduced into electrical energy using materials with magnetostrictive (Ms), piezoelectric, or shape memory effects; all of which can be deposited as thin films. In comparison to other thin film, 'smart' materials, magnetostrictive thin films offer several attractive features: a) a high energy output for remote-control actuation and communication, b) a wide range of candidate material systems—and associated process flexibility to meet end-use requirements, and c) inherent durability and robustness.

The thin film, multi-layer, architectural design for the Magnetostrictive Sensor (MsS) consists of a magnetostrictive (Ms) layer (e.g., FeCo, FeTb, or others), a transduction coil for activation/sensing, with conducting antenna patch/dielectric layers and on-board power management devices for wireless communication. To further increase response sensitivity, increase the high temperature stability, and reduce the necessary driving current for magnetic saturation (i.e., magnetic susceptibility), Ms layers are constructed as thin multi-layer(s) of magnetostrictive amorphous alloys (e.g., FeTb, etc.) in combination with magnetically soft (high magnetization) alloys (i.e., FeCo, etc.). Since all of the components can, in principle, be engineered into a thin-film architecture, and since thin-film Ms materials have already been demonstrated in remote actuator (bimorph resonators and optical scanners) and sensor applications, important factors include: 1) optimizing these materials for non-invasive operation at high temperatures (mechanical compliance, chemical inter-diffusion, etc.), 2) reducing the necessary driving fields for remote actuation/communication, and 3) orientation of in-plane magnetic-easy axis with respect to driving magnetic field(s). Results show the improvement in magnetic properties as the selection of material and architecture of the film is evolved from a single layer of nickel to a multi-layer composite film of Fe/FeTb. It is important to note that for magnetostrictive activation, the ideal magnetic response should have low coercive force, x-intercept of forward scan, high slope (permeability), and high magnetic saturation (maximum induced field on y-axis). This type of magnetic behavior will typically result in a high output response (voltage amplitude) in a pitch-catch mode of operation. An example of a less than ideal case is the as-deposited nickel film. An initially deposited 3 μm-thick pure nickel film not only exhibits a high coercive force (32 Oe), but poor permeability as well (a stepped curve due to anomalous striped domain formation). Hence, the signal (voltage) response for these single layer films was comparatively low.

In comparison to pure nickel films, alloy films have been shown to exhibit superior magnetic characteristics. For example, the magnetic response of a representative FeCo alloy exhibits a much more favorable in-plane anisotropy with high permeability in comparison to pure nickel; however, the coercive field (>40 Oe) is of the same magnitude as nickel. Hence, the overall signal actuation response is similar to that of pure nickel films. However, the addition of vanadium to FeCo and the use of a "seed" layer of Ta or Cu, results in a considerable reduction in the coercive force (from >40 Oe to <3 Oe).

Composite, Multi-layer Thin-Film Development

Figure 11:
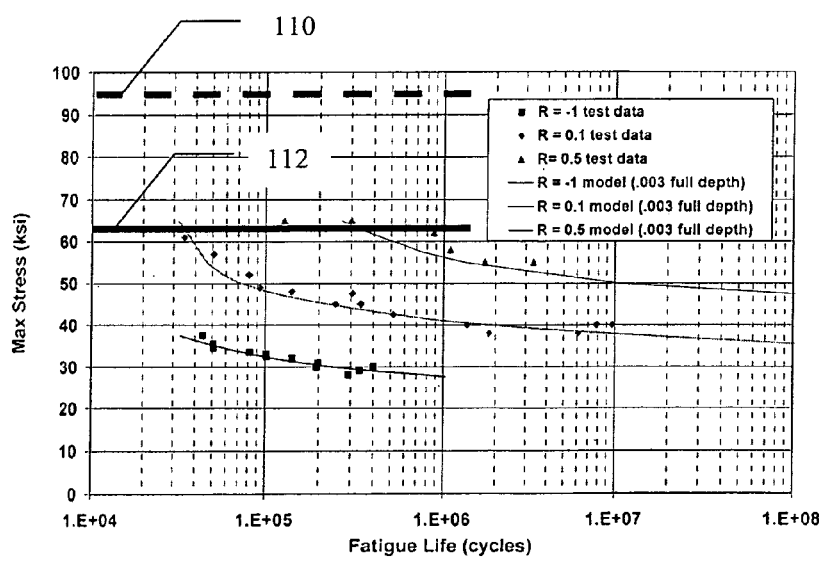
FIG. 11 is a logarithmic plot showing a comparison of FeCo thin-film de-lamination strengths with Ti-6Al-4V (a conventional fine grain titanium alloy) fatigue strengths at various load ratios.

As described above, the use of alternating layers of a high magnetization (soft) layer of FeCo, and a high magnetostrictive layer of FeTb, not only enhances the efficiency of the magnetoelastic response but also improves the interface stability at high temperatures by minimizing the driving force for nucleation and subsequent interdiffusion. An example of the improved thermal stability of the "engineered" multi-layer configuration is shown in FIG. 11 where the coercive field was reduced to less than 10 Oe for a FeCo/FeTb multi-layer stack. The multi-layer film was then annealed at 250° C. for more than 4 hours and the stability of the film was verified using x-ray reflection measurements; the periodic peaks are caused by reflections from the layered structure and the constancy of the response before and after the anneal demonstrates the stability of the stack.

Generation and Detection of Guided Waves with Thin-Films

Guided waves are mechanical, or elastic, waves in ultrasonic and sonic frequencies that propagate in a bounded medium, such as a pipe, plate, or shell, parallel to the plane of its boundary. The wave is termed "guided" because it travels along the medium guided by the geometric boundaries of the medium and the geometry has a strong influence on the behavior of the wave. In contrast to ultrasonic waves used in conventional ultrasonic inspections that propagate with a constant velocity, the velocity of guided waves varies significantly with wave frequency and geometry of the medium. This is referred to as dispersion. In addition, at a given wave frequency, the guided waves can propagate in different wave modes and orders. Although the properties of guided waves are complex, with judicious selection and proper control of wave mode and frequency, the guided waves can be used to achieve volumetric inspection of a large area of a structure from a single sensor location. One judicious approach is to choose a mode that does not have significant dispersion in the frequency range of interest. In the current work, the horizontally polarized shear wave mode is chosen because it is basically non-dispersive. This means that the wave travels in the material under inspection at a constant velocity.

Guided waves can be generated by using piezoelectric or magnetostrictive sources. Piezoelectric sources cannot be used at high temperatures (i.e. above about 200° F.). In contrast magnetostrictive sources can work at temperatures close to their Curie temperatures (in certain instances as high as 1200° F.). The magnetostrictive sensor generates and detects guided waves. For wave generation, it relies on the magnetostrictive (or Joule) effect; the manifestation of a small change in the physical dimensions of ferromagnetic materials—on the order of several parts per million in carbon steel—caused by an externally applied magnetic field. For wave detection, it relies on the inverse-magnetostrictive (or Villari) effect which is a change in the magnetic induction of ferromagnetic material caused by mechanical stress (or strain).

As discussed above, the Curie temperature can often be increased as the material moves from the bulk form to an engineered thin film. Previous work has utilized nickel foil (on the order of 125 microns thick), which has a Curie temperature of approximately 600° F.

Data on initial films that were 3 to 12 microns thick has demonstrated that guided waves could be generated. These indications were determined from data collected from thin films applied to titanium plate using the pitch-catch mode. The source in this instance is a 125-micron nickel foil and the thin-films are used as receivers. Tests have been run with a 12-micron thin film nickel on a ½ inch thick titanium plate, 7-micron thick films on ⅛ inch and ½ inch thick titanium plate, and a 3-micron thick thin film on a ⅛ inch and ½ inch plate. Even though these thin films were not optimized, the evidence shows that thin films can detect guided waves. This type of data has been observed for frequencies ranging from 250 KHz to 1000 KHz.

The Sensor Structure

Figure 3:
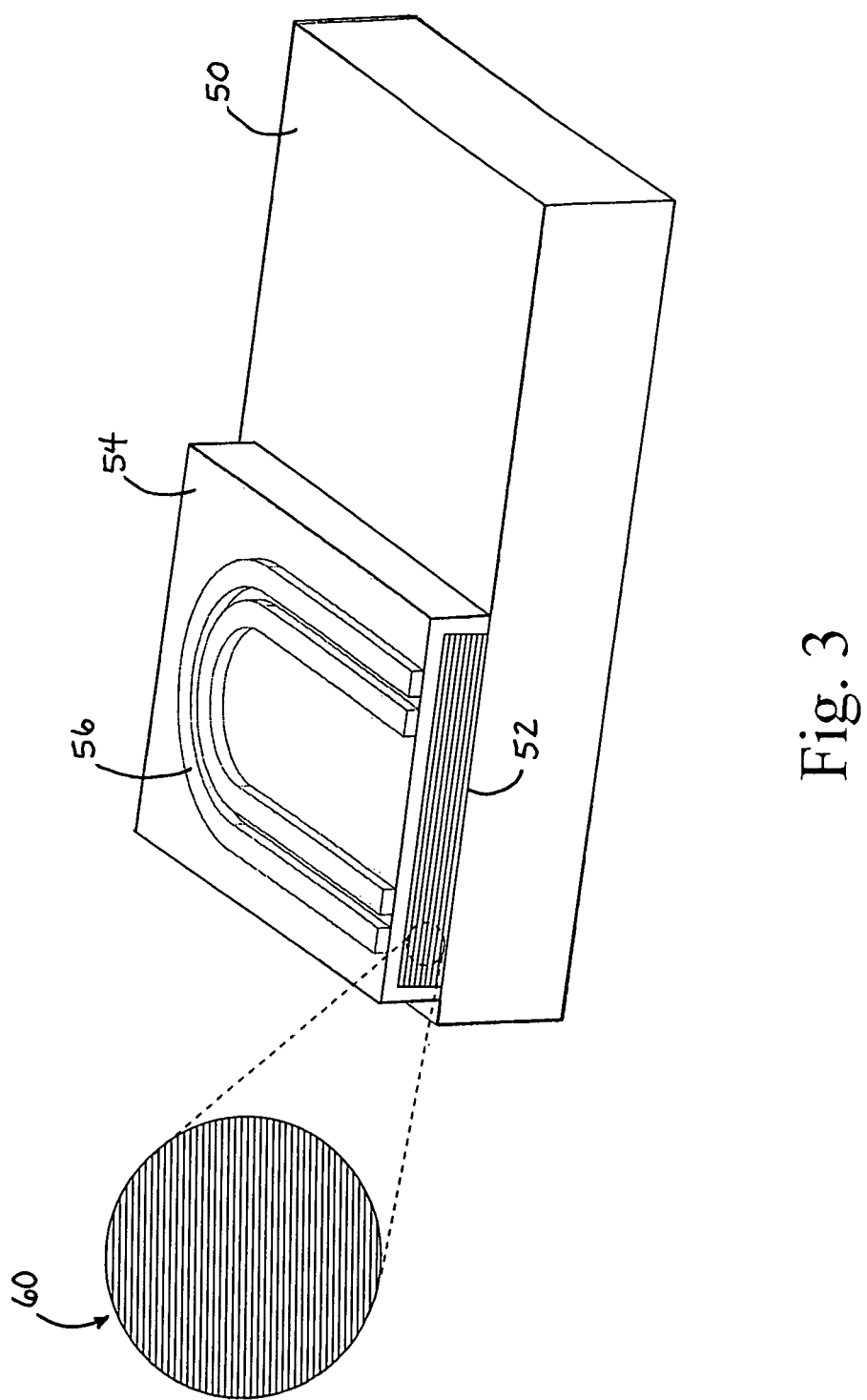
FIG. 3 is a partial cross-sectional view of the thin-film sensor of the present invention, including the planar coil component of the sensor.
Figure 4A:
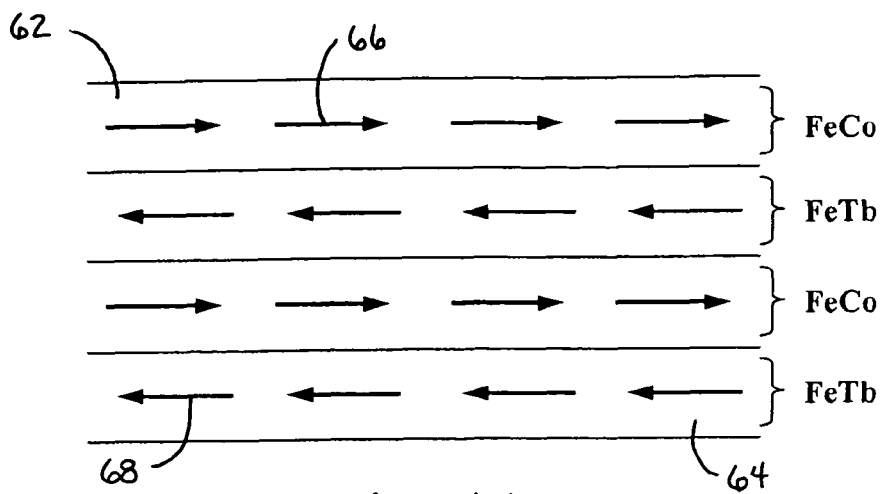
FIGS. 4A-4C are graphic representations of the spin orientations in the FeCo/FeTb multi-layer structure.
Figure 4B:
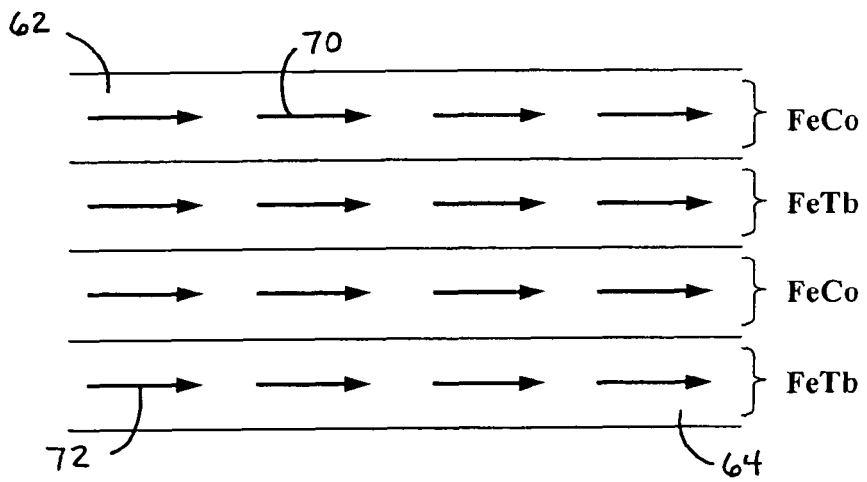
Figure 4C:
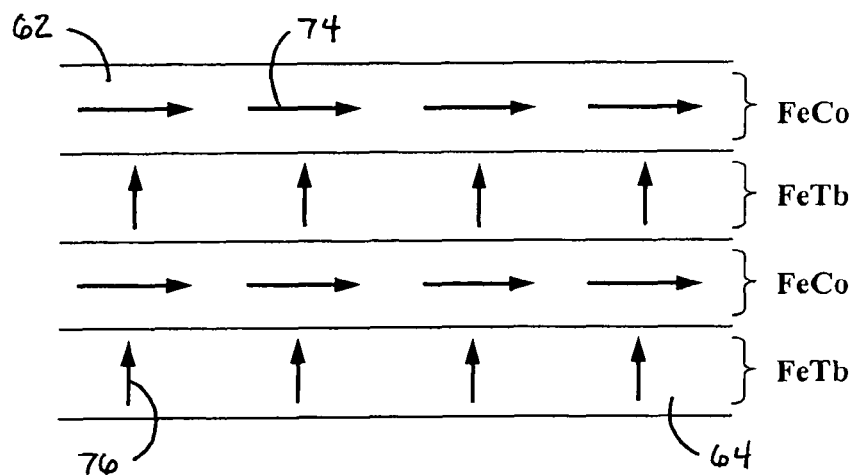

A primary component of the system of the present invention is the multi-layered thin-film sensing material. As illustrated in FIGS. 3 & 4, this multi-layered thin-film consists of alternating FeCo (crystalline iron cobalt) 62 and FeTb (amorphous iron terbium) 64 layers, which are each nominally 10 nm thick. FIGS. 4A-4C are graphic representations of the spin orientations in the FeCo/FeTb multi-layer structure where FeCo (iron cobalt) is the "soft" layer 62 and FeTb (iron terbium) is the "hard" layer 64. FIGS. 4A-4C show; (A) anti-parallel and in-plane 66 & 68, (B) parallel and in-plane 70 & 72, and (C) in and out-of-plane orientations 74 & 76. Typically 320 individual layers (see 60 in FIG. 3) are deposited giving a total film 52 thicknesses in the range of 3-4 μm. An oxide layer ($Al_2O_3$) 54 is also deposited on top of the nano-layered thin-film 52 to provide protection from the operating environment as well electrical insulation for the metallic coil 56 which is positioned on top of the oxide layer 54 as shown, and provides the electrical-to-magnetic transduction. This multi-layered, thin-film architecture has been demonstrated to provide numerous benefits: 1) high actuation efficiency and low power requirements for wireless activation and communication, 2) achievement of low mass, low profile by eliminating the use of a bulky permanent magnet magnetic biasing, and 3) thermal stability at elevated temperature by eliminating re-crystallization and suppressing diffusion.

The multi-layer magnetostrictive thin-film sensor of the present invention consists of a soft magnetization layer (i.e., FeCo with high saturation magnetization) in combination with a hard magnetization layer (i.e., FeTb with high magnetostriction); for the purpose of establishing a nano-composite film with high magnetostriction at low actuation (driving) B-fields (soft behavior). Performance is related to individual film thickness which in turn is related to the "ferromagnetic exchange length". In other words, at thicknesses below the exchange length, domain wall formation is suppressed and actuation occurs at the magnetic spin (moment) level (an average of the two individual layer properties). Although layers typically couple anti-parallel at these length scales, overall magnetization is set by the thickness ratio, that is, as a function of increasing thickness of the soft magnetic layer (with constant hard layer thickness), saturation magnetization, Ms, for anti-parallel coupling first decreases and then increases up to a value nearly equal to the case for parallel coupling.

If the individual layer thickness is increased above the minimum for domain wall formation, the magnetic polarization curve exhibits a 2-stage response (a different slope in the low field and high field regions) with the soft magnetic layer responding in the low field region and the hard magnetic layer responding at higher fields. To show the feasibility of the present invention layer thicknesses between 3 to 15 nm were investigated, although evidence has shown that with thicknesses up to 25 nm a corresponding onset of 2-stage behavior occurs. For individual layer thicknesses less than approximately 3 nm-5 nm, there is evidence to indicate the properties of the diffuse interphase region can begin to control magnetic coupling and subsequently, overall performance of the structure.

Although a low magnetic saturation field is desirable (i.e., low coercive field and high permeability), the evidence has not yet shown how layer thickness (for a constant ratio below the domain wall width) in a composite, multi-layer structure affects coercive force, $H_c$, and magnetic saturation field, $H_s$, since to a first order, spin orientation is assumed to be fairly uniform within an individual layer, whether it be the soft FeCo or hard FeTb layer. In other words FeCo, with its high magnetization, provides the high saturation magnetization and soft magnetic response whereas the FeTb, with its high magnetostriction, provides the gain to the actuation response. Management of spin orientation within the individual layer of a composite structure, however, is important to overall multi-layer performance. In particular, spin orientation with respect to the plane of the film and the applied magnetic field directly affects the overall output response of a multi-layer magnetostrictive film and is directly affected by each of the processing parameters discussed in more detail below.

The Sensor Method of Manufacture

It is first important to characterize the concept of spin orientations within a multi-layer structure and its affect on actuation response. The first factor to consider is the ease of movement or rotation of the spin and is typically characterized by the magnetic polarization loop. In general, a low coercive field, $H_c$, in combination with a low magnetic saturation field, $H_s$, is indicative of low anisotropy with spins orienting easily and rapidly along the applied magnetic field direction. Spins that rotate easily, although crucial to insuring low magnetic actuation fields, do not necessarily correspond to maximum displacement. The key is the initial orientation of the spins within the multi-layer structure as the initial orientation of spins, not only have a direct impact on the output strain or displacement of the film, but the resulting remnant or retentive field within the structure as well; i.e., the response to a fixed magnetic bias field. In applications where a permanent magnet cannot be used to pre-align spins, it would be desirable to have a film that could establish a preferential orientation to the spins that maximizes strain (displacement) under an applied field.

In general, for positive magnetostrictive materials (FeCo and FeTb), induced tensile stresses promote in-plane spin orientations (distribution) within a thin film whereas compressive stresses promote out-of-plane spins or spins perpendicular to the plane of the film. Since in most thin-film actuator applications, the applied magnetic field is in the plane of the film, the approach is to create spins that are not only in the plane of the film but perpendicular to the applied field. For a typical multi-layer film with anti-parallel coupling, the spin orientation (designated by arrows 66 & 68) would appear as in FIG. 4A for each of the individual layers 62 & 64. Depending on processing parameters, spins could also be oriented in-plane and parallel (shown in FIG. 4B) as well as a mixture of in-plane and out-of-plane orientations (shown in FIG. 4C).

Figure 5A:
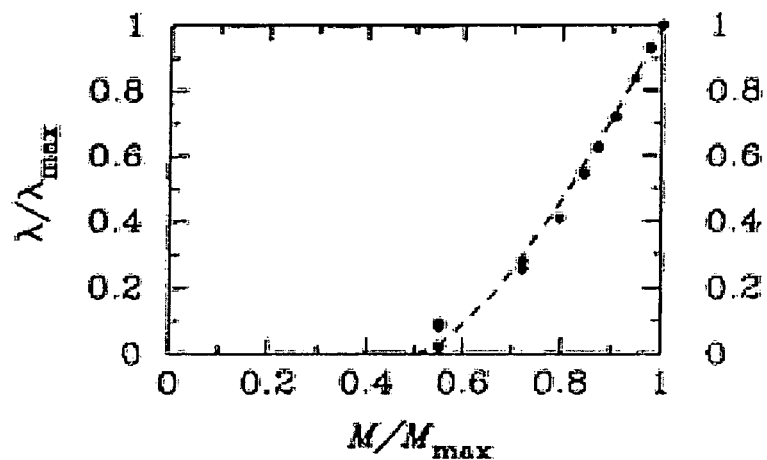
FIGS. 5A & 5B are graphs of normalized magnetostriction vs. normalized magnetization for in-plane (FIG. 5A) and perpendicular (FIG. 5B) anisotropy.
Figure 5B:
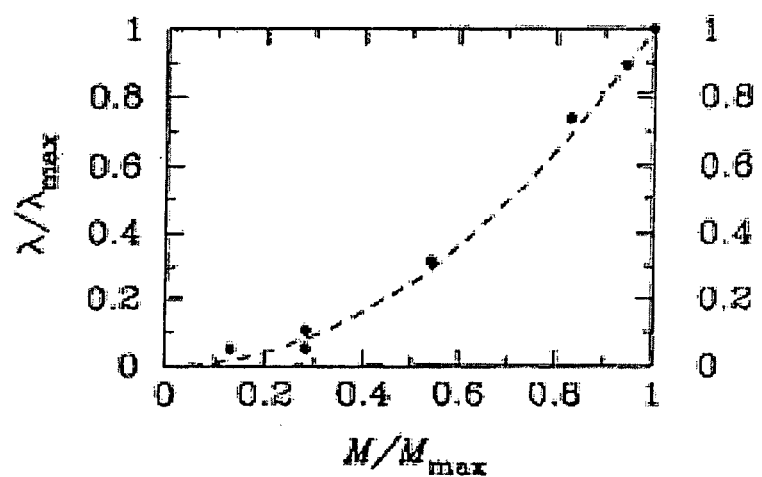

Magnetic anisotropy is typically produced through a dipole-dipole interaction and the local crystalline-electric-field gradient through spin-orbit coupling. As a consequence of a higher density of neighboring atomic distribution in the film plane, i.e. dense films with compressive stresses, the electron angular momentum tends to be aligned perpendicular to the plane and therefore magnetization perpendicular to the plane. With respect to maximizing the change in magnetostriction or displacement, orientation of the magnetic field with respect to the distribution of spin orientations is critical. For example, a magnetization process only caused by motion of 180° spins cannot lead to any magnetostriction. In cases shown in FIGS. 4A & 4B above for in-plane spins, if the spins and the magnetic field are oriented as shown in the plane of the page without any orientation out of the page, then there would be very little magnetostriction. In this case, there is some in-plane anisotropy and these types of films would exhibit high magnetostriction at low fields due to easy rotation of spins in the isotropic plane even though the 180° spins don't contribute much to magnetostriction. According to sources in the prior art, the motion of 180° domain walls leads to a magnetization of $M_{max}/2$ without any magnetostriction. Ideally a magnetization process due to motion of 90° spins (oriented into or out of the page for shown in FIGS. 4A & 4B) will induce a larger change in magnetostriction with easy rotation of spins. In contrast, films with perpendicular anisotropy, such as shown in FIG. 4C, require higher applied fields in order to obtain the same in-plane magnetization and magnetostriction although the overall magnetostriction would be higher than in shown in FIGS. 4A & 4B. Predicted responses for in-plane and out-of-plane magnetostriction are shown in FIGS. 5A & 5B respectively.

Figure 6:
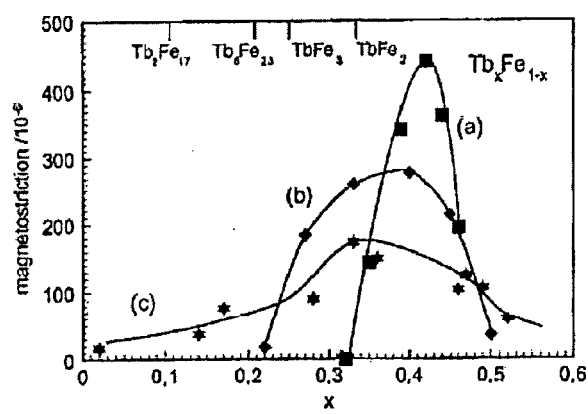
FIG. 6 is a graph of magnetostriction vs. terbium content for different deposition methods.

Thin films of amorphous FeTb prepared by most vapor deposition methods possess a strong intrinsic uni-axial magnetic anisotropy perpendicular to the film plane reflecting some sort of anisotropy built in during the growth process; i.e., presumably at the local cluster level (thermal, strain, etc.). This uni-axial anisotropy varies with FeTb composition, peaking at a concentration of around 26-28 atomic percent and then decreasing in a predictable linear fashion at concentrations above 35%. Some variation in easy axis orientation occurs as the concentration is varied above and below 22 atomic percent Tb. At Tb concentrations greater than approximately 32%, magnetostriction increases and then peaks at a concentration around 42% for DC magnetron sputtered films with an applied in-plane magnetic field as shown in FIG. 6. (It is important to note that the prior art shows that zero magnetostriction occurs for Tb concentrations less than 32% in DC magnetron sputtered films). Evaporated and RF sputtered FeTb films exhibit a much broader magnetostrictive response as a function of composition with reasonable responses below 30% Tb.

In summary, a structure that facilitates easy spin rotation would yield a quick (movement at high frequency) response at low magnetization fields; anisotropy would tend to be low in this type of situation and therefore a magnetic bias field would be required to induce preferential alignment prior to actuation. In contrast, a structure that has higher anisotropy in the hard layer, in particular spins oriented perpendicular to the plane of the film (case (c) above) would require higher overall activation fields although the overall actuation may be greater and the higher anisotropy would tend to preferentially orient spins without the need for a magnetic bias field.

Based on the above strategy, FeTb/FeCo multi-layers can be produced from compound and tiled targets using dual DC magnetron sputter sources. The specific process parameters (independent variables) used to fabricate these films are as follows:
RF Bias
Source Power Settings (Power/Voltage)
Thickness (individual layer, total number of layers, ratio, etc.)
Layer composition
Surface pre-treatment (ion clean, "seed" layer, etc.)
Sputter/Base Pressure (throttle position and gas flow)
Substrate-to-source distance, Angle-of-incidence
Magnetic Bias
Substrate Temperature The present invention therefore addresses a method for manufacturing an engineered, monolithically integrated, multi-layered (nano-composite), thin-film structure for flaw detection and monitoring, which consists of a thin-film multilayer magnetostrictive layer, a thin-film electrically insulating or dielectric layer, and a thin-film activating layer, such as a planar coil, that includes: (a) magnetron sputtering of alternating layers of a high (hard) magnetostrictive material (iron/rare earth or similar alloy) and a high magnetization (soft) material (FeCo or similar) directly onto sensing platform or onto flexible backing substrate that can later be affixed to sensing platform, (b) composite magnetostrictive layer properties, such as magnetostriction coefficient, saturation magnetization, and Curie temperature (thermal stability), that are engineered by adjusting layer thickness (2-50 nm), soft/hard layer ratio (typically greater than 1) and sputtering deposition parameters (with and without ion assist and/or RF sample bias) with minimum total layered composite thickness such that losses due to skin depth effects are minimized (typically greater than 3 microns), (c) composite magnetostrictive layers that are post-annealed in a magnetic bias field or annealed in-situ as part of elevated temperature service to enhance performance, (d) a dielectric layer, such as oxide, nitride, carbide, or other, deposited over top of the composite layer using reactive magnetron sputtering (or other compatible method) to serve as electrically insulating layer and for resistance to high temperature oxidizing environments; thickness not to exceed 3 microns, and (e) an activation layer, such as conductive planar antenna coil, deposited through shadow mask directly on top of dielectric layer.

In addition, the method above may include a step where the surface of the sensing platform is treated chemically, thermally, or mechanically (or coated with adhesion promoter layer) to optimize impedance and mechanical adhesion of composite magnetostrictive film at elevated temperatures. The method may also include a step where the monolithically integrated sensor is applied to different types of sensing platforms (other engineering metals, composites, etc.) or applied to flexible (or thin) film support which is then bonded to engineering platform.

The method of the present invention may also include a step where a magnetic spin orientation is engineered as part of the manufacturing process thereby eliminating the need for magnetic biasing with permanent magnets prior to activation, or during operation. Further, the method may include a step where the dielectric layer and activation layer are deposited by methods other than magnetron sputtering, such as other PVD, wet chemical, or plasma/flame spray techniques.

The method may also use other types of magnetostrictive materials (other than iron-based) to achieve specific properties or enhance actuation performance. The method may also be applied where the monolithically integrated sensor is used for other applications than flaw detection, such as temperature, strain, and other.

The Sensor Robustness

Film magnetostrictive performance and durability were optimized by following the above strategy and through manipulation of the above processing parameters based on feedback from measured magnetization (magnetic polarization), magnetostriction, mechanical stress, thermal stability and de-lamination strength. The application of the resulting films to defect detection over a range of temperatures and stresses is described below.

Figure 7A:
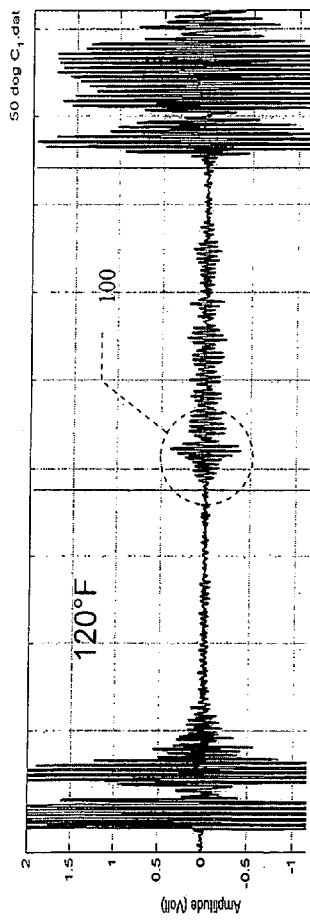
FIGS. 7A-7C are graphs of signal defect detection using the multi-layered thin-film sensor over a range of temperatures.
Figure 7B:
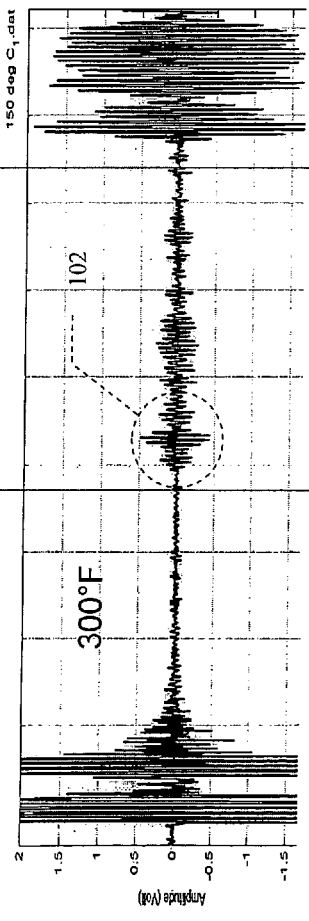
Figure 7C:
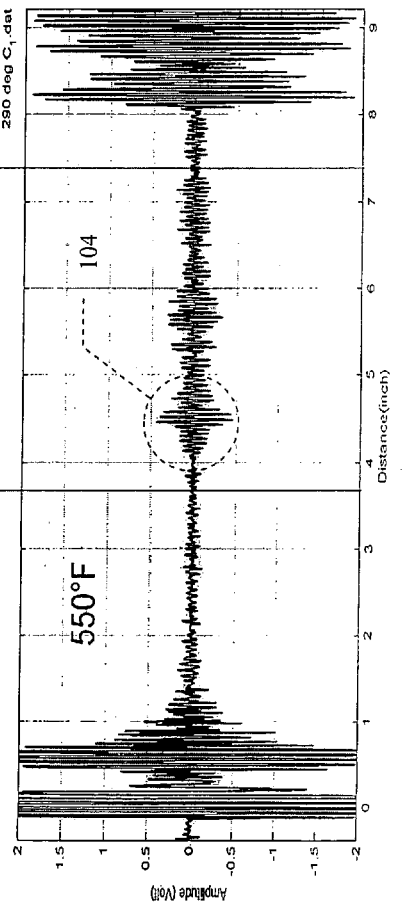

FIGS. 7A-7C show the signals obtained from a 4 µm-thick, 320 layer FeCo/FeTb film as a function of temperature. All data were obtained with the sensor deposited near the end of a 2 in.×8 in.×0.125 in. aluminum alloy plate containing a 0.060 in.×0.4 in. notch defect located about 4 in. from the sensor. The saturated signals to the left in these figures correspond to the initial activation of the sensor and the reflection from the near edge of the plate, while the large signals in the right of these figures are the reflections from the far edge of the plate. The smaller signals in the middle of these figures (circled as 100, 102 & 104), at about 4 in. on the horizontal scale, are reflections from the defect. As can be seen the defect signal is clearly evident and is about 10 times the background noise level in all cases. The fact that the amplitude of the signal does not diminish upon increasing the temperature from 120° F. to 550° F. attests to the stability of the film over this temperature range.

In addition, films were exposed to temperatures of 550° F. for hundreds of hours without observable changes in magnetization (B-H) curves, and X-ray reflections.

It is also interesting to note that the position of each reflection in FIGS. 7A-7C systematically shifts to the right with increasing temperature. This is due to the decrease in the velocity of the elastic (ultrasonic) wave propagation with increasing temperature. This temperature sensitivity results in a longer arrival time, which is interpreted as an apparent increase in distance of the reflectors from the thin film sensor when a constant velocity is assumed. This shift does not pose a problem for the monitoring of defects since it is the amplitude that is of primary interest to these measurements. This effect could also be compensated for in the signal processing by using the shift in reflections from fixed features (e.g., edges, holes) to estimate the temperature and correct for the change in wave propagation velocity. These results also demonstrate that the sensor is multifunctional and can be used to monitor temperature, as well as defects, in components.

Figure 8:
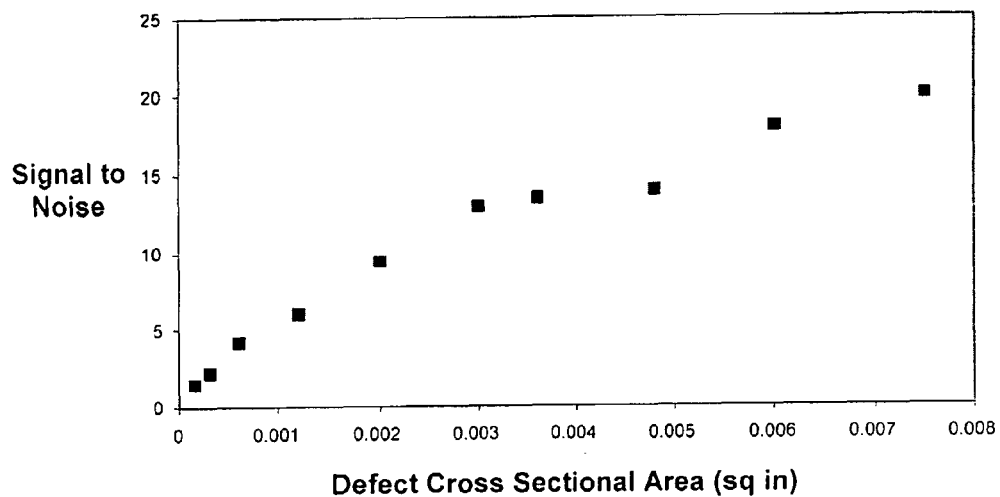
FIG. 8 is a graphic plot of the signal to noise ratio for variations in the defect cross-sectional area using the sensor of the present invention showing the sensitivity of the multi-layered thin-film sensors.

Initial experiments to characterize the flaw size detection sensitivity of the thin film sensor have recently been performed. Surface-connected, notched flaws of increasing sizes from 5 mils deep by 30 mils long (5×30 mils) to 50 mils deep by 150 mils long were successively introduced into a 2 in.×8 in.×0.125 in. plate containing a multi-layered thin-film sensor at one end about 2 in. from the defects. Results are shown in FIG. 8 in terms of defect area versus signal-to-noise ratio (SNR). The two smallest areas near the detection limit corresponded to defect sizes of 5×30 mils and 10×30 mils and exhibited SNR values of 1.5 and 2.2, respectively. In contrast, the largest defect exhibited an SNR value of about 20. The results in FIG. 8 show that the sizes being detected are about ten times smaller in size than the target sensitivities that probabilistic computations have shown to be beneficial to component reliability.

Figure 9:
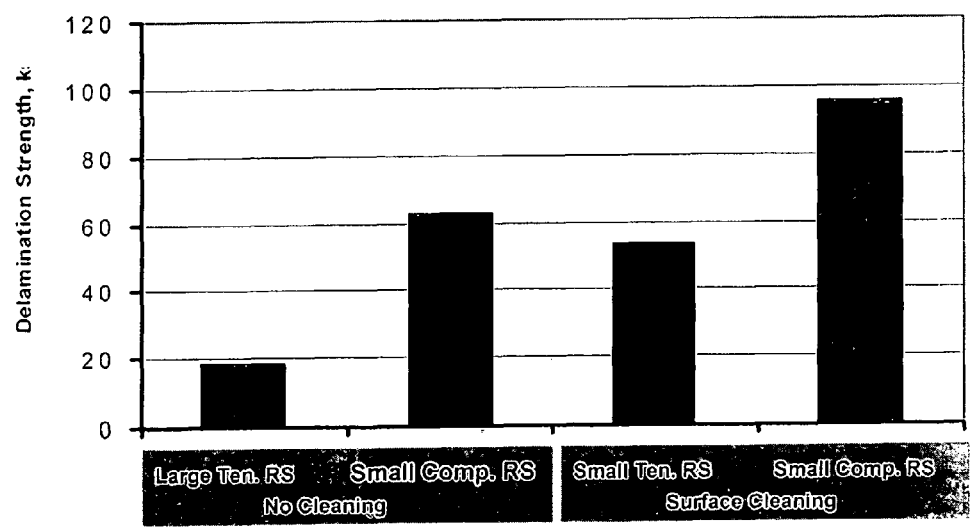
FIG. 9 is a bar chart showing the de-bond strength of a 4 µm FeCo thin-film sensor structure as a function of film processing steps.

In addition to temperature stability, it is important that sensors for on-board monitoring have adequate mechanically durable to withstand the stresses experienced by components in service. An assessment has been made of the durability of FeCo thin films on Ti-6Al-4V. As shown in FIG. 9, the de-lamination strength of 4 µm thick FeCo films is a strong function of processing parameters. As can be seen from these results in this figure, de-lamination strength can be significantly increased (up to 5 times) by sputtering to remove nascent oxides from the substrate before depositing the film, as well as by producing slightly compressive stresses in the films.

Figure 10:
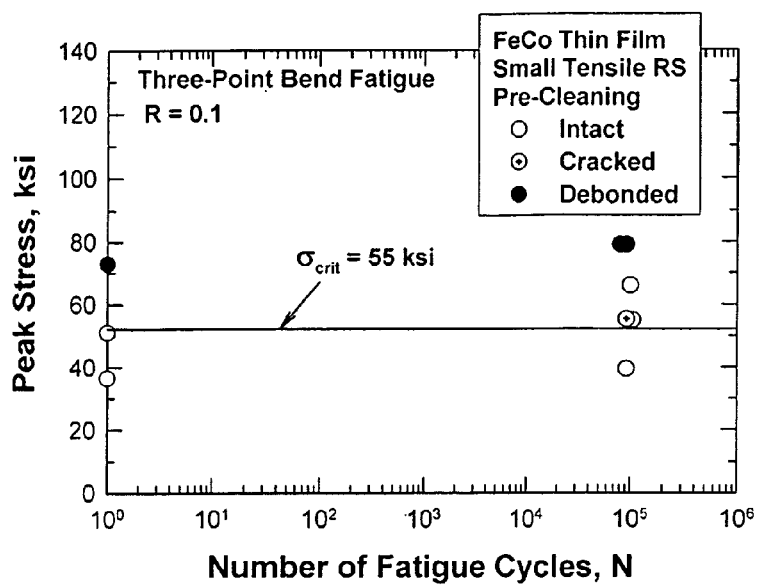
FIG. 10 is a logarithmic plot showing the de-lamination strengths of 4 µm FeCo thin-film during first half-cycle (monotonic loading) and after $10^5$ fatigue cycles.

The fatigue performance of the thin film is also of interest since many critical components are subjected to fatigue loading. FIG. 10 shows, again for a 4 µm-thick FeCo film on Ti-6Al-4V, that the fatigue strength of the film is essentially the same as the de-lamination strength (shown plotted at 1 cycle). These data indicate that the strength of the thin film is controlled by interface de-lamination and not by fatigue. This observation is not surprising since the grain sizes in the deposited thin films are typically less than 1 µm, and it is well known that fine grain size promotes high fatigue strengths.

Figure 12:
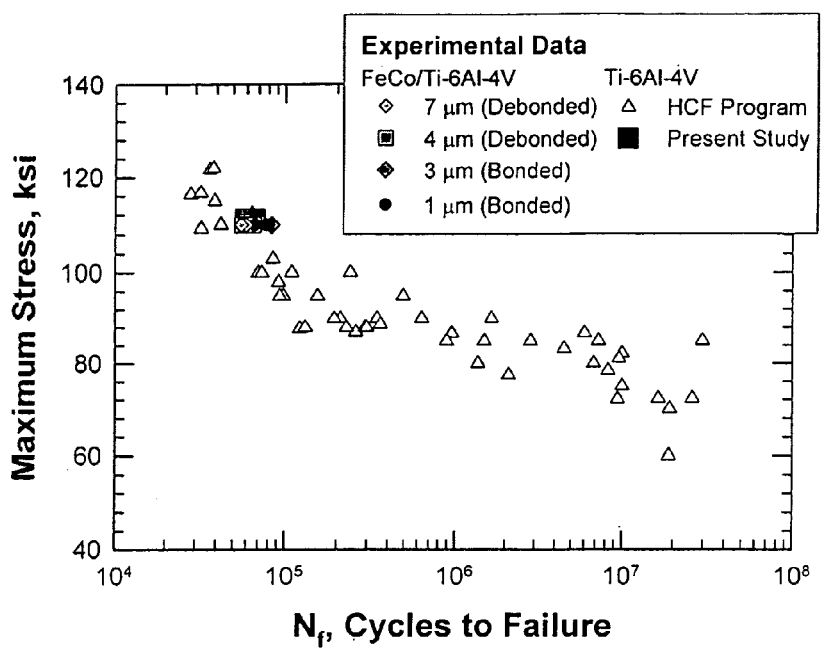
FIG. 12 is a logarithmic plot showing a comparison of fatigue strengths of Ti-6Al-4V with and without 3-4 µm thin-films.

FIG. 11 is a logarithmic plot showing a comparison of FeCo thin-film de-lamination strengths with Ti-6Al-4V (a conventional fine grain titanium alloy) fatigue strengths at various load ratios (R) obtained on notched specimens with an elastic stress concentration factor ($k_t$) of 2.4. The high de-bond strengths indicate that films can withstand typical low-cycle fatigue loading in compressor discs. FIG. 11 compares the two highest de-lamination/fatigue strengths with the fatigue strengths of notched Ti-6Al-4V coupons. As indicated, the strength of the film exceeds the strength of the Ti-6Al-4V in the fatigue regime of interest to turbine discs, which is beyond $10^5$ cycles. It should be pointed out that the results in FIG. 12 are plotted in terms of the maximum nominal stress (not the concentrated stress at the notch) since the sensors would be located several inches or more away from the fatigue critical location in components and thus would not experience the concentrated stresses. Film de-bonding levels are shown for Comp. RS plus cleaning at 110, and for simple Comp. RS at 112.

The fatigue strength of the substrate in the presence of the thin film is also paramount importance, since the film deposition process must not degrade the durability of the underlying material/component. FIG. 12 is a logarithmic plot showing a comparison of fatigue strengths of Ti-6Al-4V with and without 3-4 µm thin-films. Invariance of the fatigue strength with and without the film demonstrates that the film deposition process is not detrimental to the titanium alloy substrate. FIG. 12 compares the fatigue strength (at about $10^5$ cycles) of Ti-6-Al-4V bend specimens with and without thin films. These results are essentially indistinguishable. Baseline results generated on the same heat of materials using tension specimens are also shown for comparison. Although the latter comparison indicates higher fatigue strengths for the specimens with thin films, this difference is likely due to the well-known tendency for bend specimens to exhibit higher fatigue strengths than tensile specimens due to the stress gradient in the specimen. Nevertheless, the conclusion is that the FeCo thin films do not degrade the fatigue strength of the Ti-6-Al-4V substrate.

Figure 13:
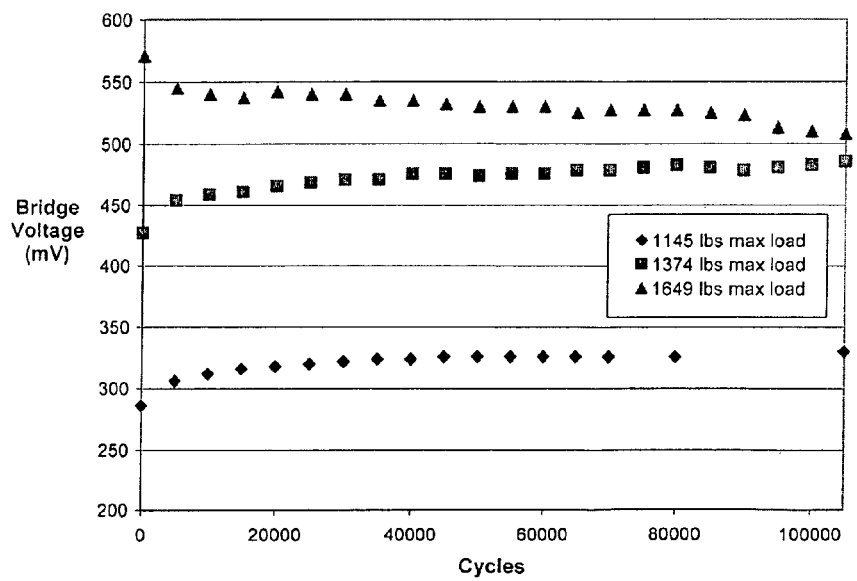
FIG. 13 is a graphic plot of strain signals from thin-film structures during fatigue testing to 100,000 cycles at maximum applied stresses of 79 ksi (top curve), 65 ksi (middle curve), and 55 ksi (bottom curve) (ksi=thousands of pounds per square inch).

Fatigue experiments were also performed while monitoring the performance of the thin-film in the inverse mode. This mode is the inverse process from that described above for launching elastic waves to interrogate the material for damage. Specifically, the applied stress in the substrate caused a change in the magnetic flux in the film, which is in turn sensed by the coil as an electric current. In this mode, the film functions similar to a strain gage. However, the resulting voltage is due to the inverse magnetoelastic effect and not due to a resistance change as in conventional wire strain gages. The voltage outputs from the film are shown in FIG. 13 as a function of applied fatigue cycles at increasing levels of maximum applied stress. At low stress (55 ksi), the film response exhibits an initial transient before stabilizing for the remainder of the test to $10^5$ cycles. At the intermediate stress (65 ksi), the response is initially similar to that at the lower stress but subsequently continues to increase slightly throughout the test. This increased output throughout the fatigue test is hypothesized to be due to the evolution of slip in selected grains that are favorably oriented with respect to the direction of applied stress. At the highest stress (79 ksi), de-lamination of the film was observed, and although the film continued to respond, the magnitude of the signal decreased throughout the experiment. The continued response of the film is due to the fact that de-bonding begins locally and propagates over increasing regions of the film. Thus, the film continues to respond but the signal strength decreases as less and less film is in intimate contact with the substrate. Two conclusions can be drawn; first, the magnetostrictive thin films can be employed to monitor strain—another indication of their multi-functionality, second, the films give clear indications of de-bonding by decreasing strain response. In this regard, the amplitude of reflected elastic waves from defects and interfaces has also been observed to decrease following the onset of de-bonding. These features can be used during data processing to identify a malfunctioning sensor. The inverse magnetoelastic response associated with changing stress in the component is not expected to alter the crack detection process since the mechanical loading occurs at much lower frequencies than the frequency (500 kHz to 1 MHz) used to interrogate the material.

The Wireless Signal Acquisition Methodology

The method of the present invention also involves the use of a wireless communication system that can be used to transmit the data acquired by the thin film multi-layer sensor to a receiver antenna near or within the component under interrogation. In addition, the method may employ passive wireless communication of the response signal from the magnetostrictive sensor.

The system of the present invention includes an RF backscatter modulator circuit with high fidelity for communicating analog response signals from a magnetostrictive sensor and employs a method for coupling RF signals from an antenna on a stationary component to an RF backscatter modulator on the rotating component.

To assess the feasibility of wireless communication with a thin-film magnetostrictive sensor within a rotating component (in this case, a turbine engine core), two types of experiments were performed. The first was designed to characterize the radio channel between the sensor, which would be deposited on the surfaces of the rotating engine discs, and an interrogating antenna located at one or more fixed positions within the engine casing. The second was designed to characterize the performance of radio backscatter technology, in particular signal dynamic range, which affects sensor sensitivity.

Both experiments utilized two different radio backscatter ID tags, which operate with an illumination signal of approximately 2.45 GHz and produce a modulation signal that is approximately 100 kHz offset from the illumination frequency. These tags were designed to be as simple as possible to facilitate their migration to a thin-film form factor to enable operation within the elevated temperature environment of turbine engines.

Figure 14:
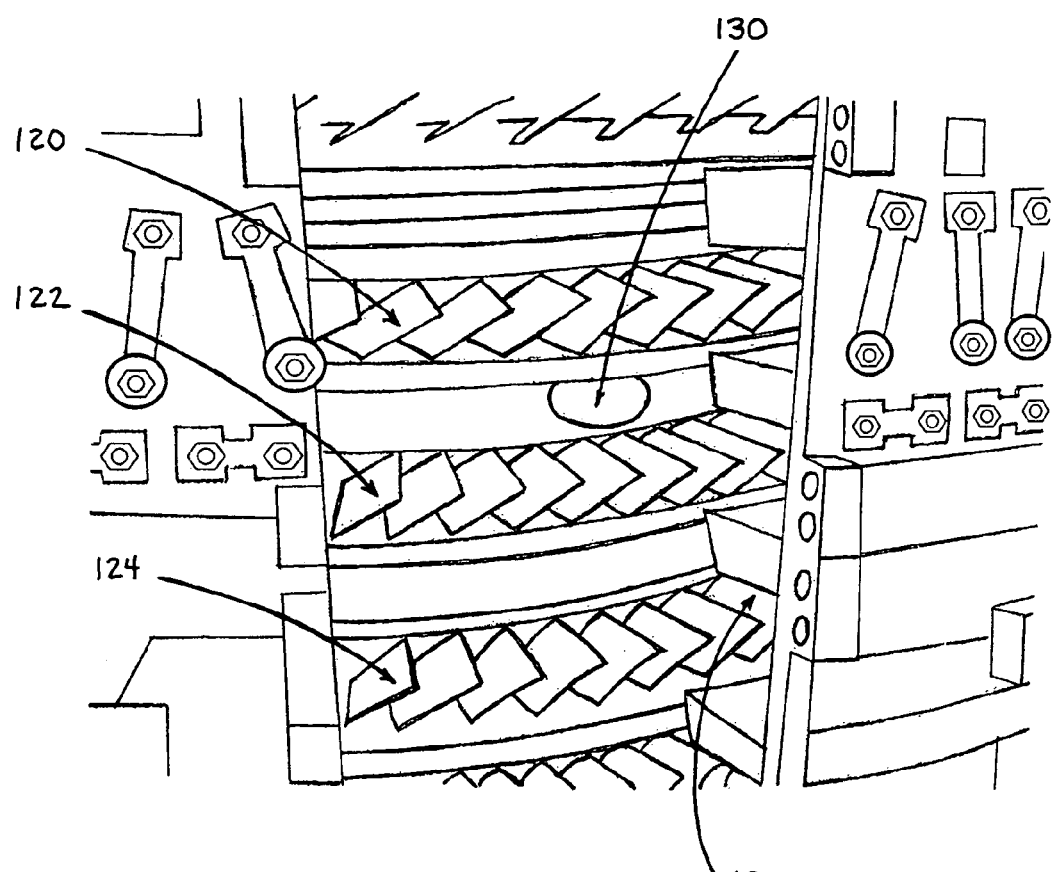
FIG. 14 is a perspective view of an open split turbine casing showing a patch communications tag positioned on the rim region of the $7^{th}$ stage compressor disc of a turbine engine.

In the first set of experiments the two tag types were placed inside an enclosed section of a military engine core as is depicted in FIG. 14 and tag return signals were monitoring with an external antenna. One tag type incorporates a patch antenna (printed metallization on a circuit board) while the other is a dipole type with protruding wires. The patch tag is enclosed in a plastic disc case that is 2.2" diameter and 0.33" thick. This tag 130 was placed on the $7^{th}$ stage compressor disc 122 rim surface of a military engine above the seal as shown in FIG. 14. The dipole tag is much smaller (1"×0.5"×0.2" with dipole wires extending another 0.75" on each side of the 1" dimension), and was installed between two of the blades on the $8^{th}$ compressor stage 124. In each case, the tags were taped into place to keep them from shifting during the course of measurements.

External antennas were configured for both radial and axial wireless access to the tags. For radial access, an existing 7/16" diameter access port 126 located between the $7^{th}$ and $8^{th}$ stages 122 & 124 of the compressor was utilized. The external antenna for radial access consisted of a one-quarter-wavelength coaxial cable stub formed by simply stripping back the outer jacket and braided cable shield approximately 0.8" from one end of a coaxial cable leaving just the center conductor and dielectric. The exposed stub end was covered with electrical tape to prevent shorting to the engine surfaces when inserted into the access port. Radial measurements were taken with the antenna probe inserted into the access port in two manners: 1) with it straight in, perpendicular to the casing wall, and 2) with it bent at right angle after insertion, running parallel to the casing wall. For axial access, a spiral cavity-backed antenna was positioned directly above the $4^{th}$ stage blades pointing downward toward the $5^{th}$ and subsequent stages.

Measurements of the tag return signal modulation level were taken at 30-degree increments clockwise around the full circle (12:00, 1:00, 2:00, etc) by manually rotating the bladed disc assembly. For example, at 12:00, the antenna is directly adjacent to tag, whereas at 1:00, the tag is rotated roughly 30 degrees clockwise with respect to antenna as viewed when facing the $4^{th}$-stage compressor side of the engine.

Figure 15:
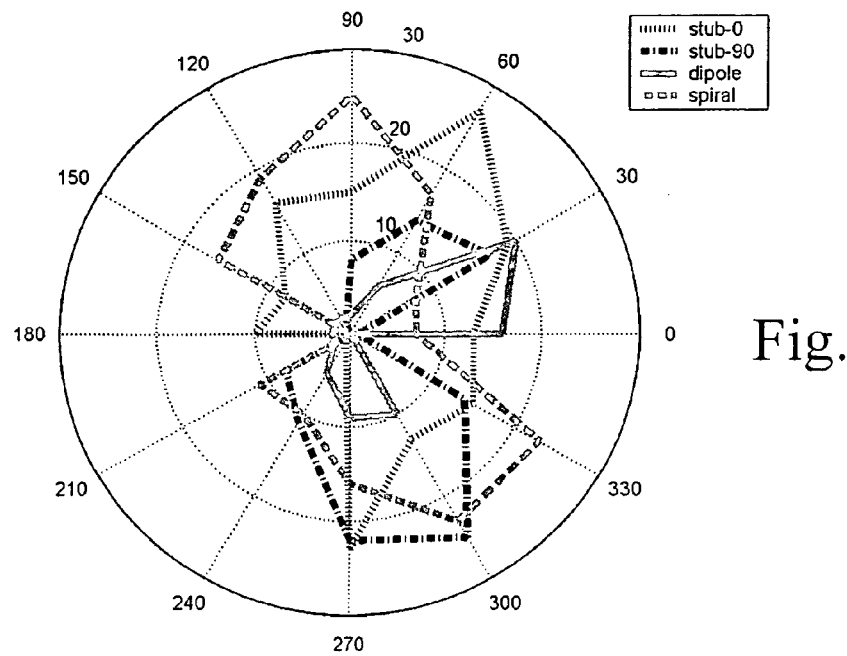
FIG. 15 is a polar coordinate plot of return levels (above noise floor) from a wireless backscatter communication tag with various types of antennae.

The polar plots in FIG. 15 illustrate the azimuth responses for four different test cases as follows:

Test Case 1, "Stub-0": Patch Tag, External Stub Antenna inserted into the radial access port with the Stub straight in line with the access port such that it runs perpendicular to the casing wall.

Test Case 2, "Stub-90": Patch Tag, External Stub Antenna inserted into the radial access port with the Stub bent at right angle such that it runs parallel to the casing wall.

Test Case 3, "Dipole": Dipole Tag, External Stub Antenna inserted into the radial access port with the stub bent at right angle such that it runs parallel to the casing wall.

Test Case 4, "Spiral": Patch Tag, External Spiral Cavity-Backed Antenna positioned axially above the $4^{th}$ compressor stage facing downward toward subsequent stages.

The above results show that wireless communication is feasible within the complex geometry of the turbine engine core using radio backscatter tags located on the disc rim surfaces, blade attachment points, or blades, and an external antenna positioned radially between stages from the existing built-in access ports. Axial propagation across multiple stages is also feasible meaning that an access port is not required for each stage. Although the tags could not be read from some azimuth positions, this may be overcome by higher illumination power and/or selection of a different illumination frequency. The tags available for testing were only operable near 2.5 GHz, so other frequencies were not investigated at this time. From another perspective, less than 360-degree azimuth coverage could benefit the system by providing a means of separating responses from multiple sensors.

To characterize the dynamic range and fidelity of communication signals from these same radio backscatter ID tags, a test setup was configured in an RF anechoic chamber consisting of a modulation source, a backscatter tag (antenna plus modulator), a backscatter reader, a digitizing oscilloscope, and a spectrum analyzer. A modulation waveform is communicated over a 2.4 GHz radio backscatter link and recovered for display on the oscilloscope or spectrum analyzer. The backscatter tag was placed at a distance of two meters from the reader. The reader was operated with its antenna panel orthogonal to the floor and facing the tag.

For dynamic range characterization, the waveform generator was set to a 100 kHz sine wave signal. A variable 100-dB attenuator was inserted in series between the signal source and the tag in order to extend the amplitude range of the generator such that low drive levels could be reached. The spectrum analyzer was tuned to 100 kHz with a resolution bandwidth of 1 kHz and the observed signal power level was measured as a function of the drive level applied to the backscatter tag.

To assess communications performance, the waveform generator was loaded with digitally sampled data that was captured using typical magnetostrictive sensor (MsS) instrumentation. This waveform is an actual MsS signal that was obtained using an existing Ni-foil sensor that is representative of the type of signal that is anticipated for the thin-film sensor. It is the echo return signal from a nickel foil MsS probe, which has been stimulated by an inductively-coupled short pulse (i.e., a few cycles) of a 128 kHz sine wave. The waveform recovered via the backscatter link was observed on the digital oscilloscope and compared with the modulating signal.

Figure 16:
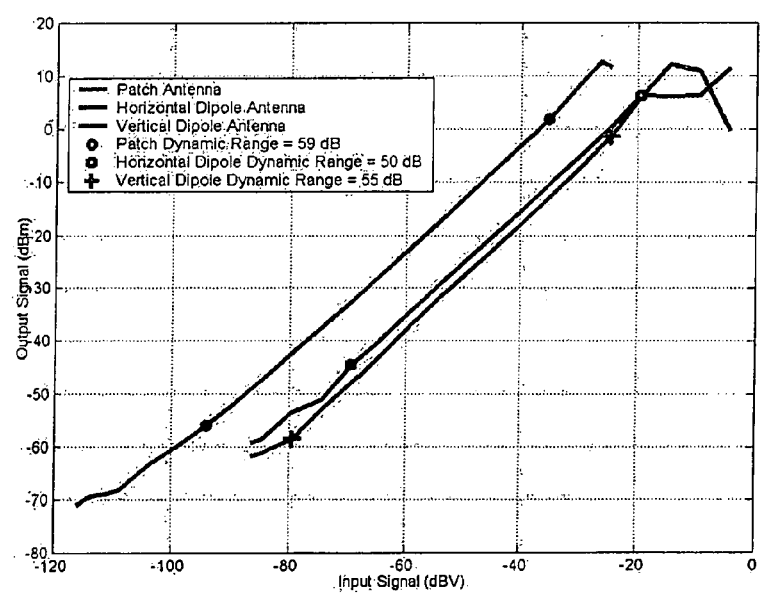
FIG. 16 is a graph of the input signal vs. the output signal for various antennae arrangements showing the wireless backscatter communications dynamic ranges for each.
Figure 17A:
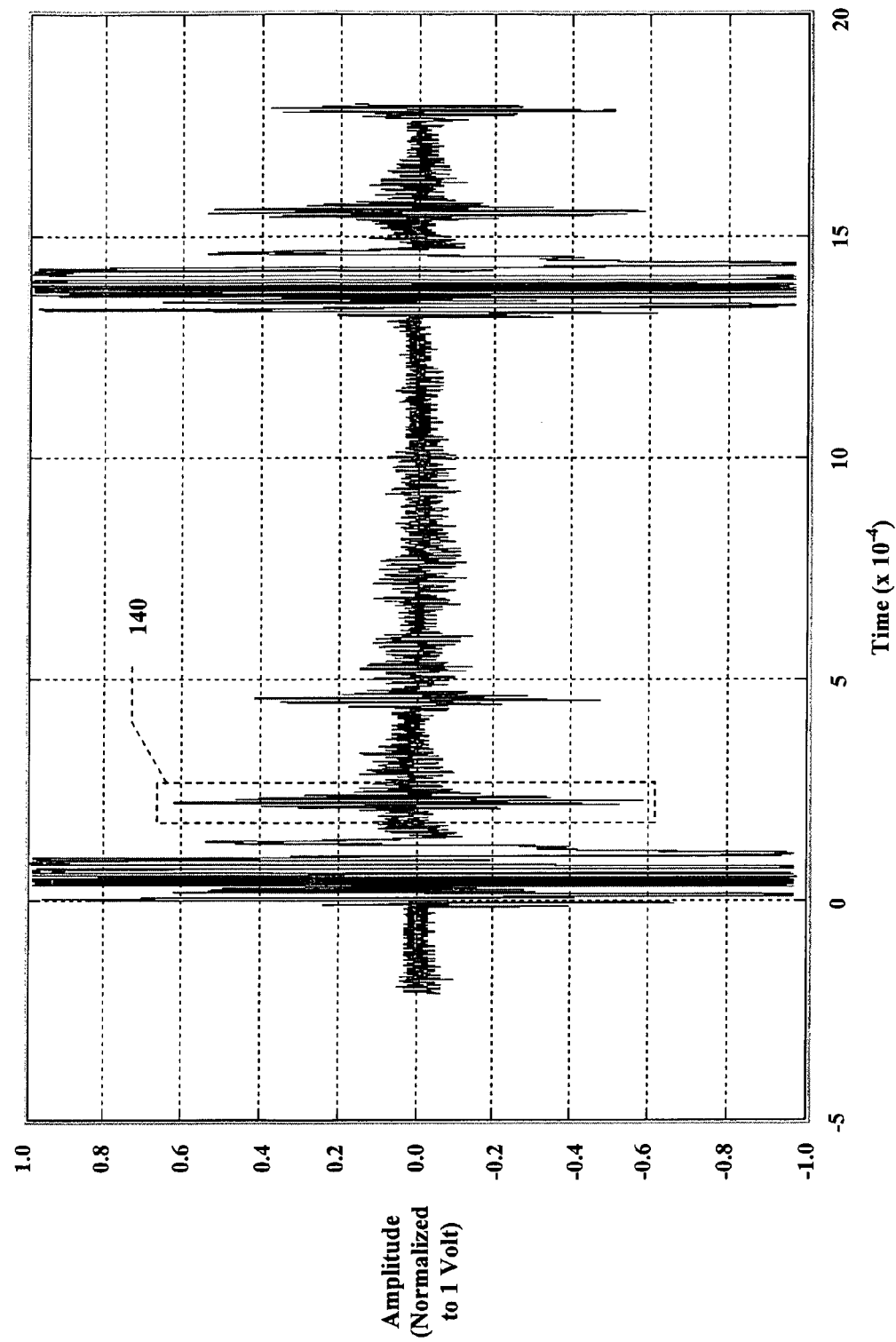
FIGS. 17A & 17B are signal graphs showing a magnetostrictive sensor (MsS) waveform communicated wirelessly via backscatter link.
Figure 17B:
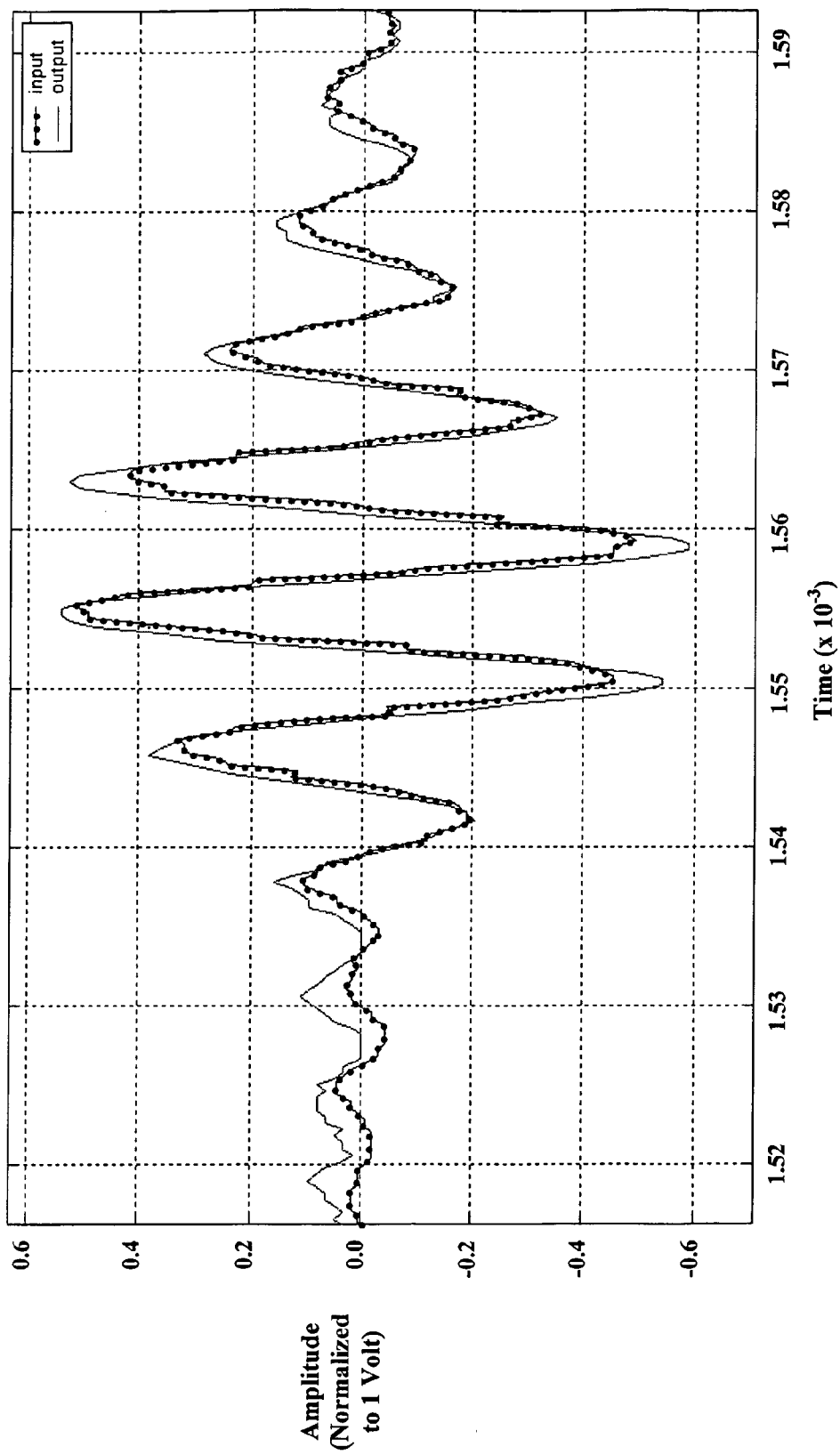

A plot of modulator drive level (input) versus recovered signal level (output) is shown in FIG. 16, illustrating the linearity or dynamic range of the backscatter communications channel. Separate plots are overlaid for direct comparison of the different backscatter tag antenna configurations that were tested (patch, horizontal dipole, vertical dipole). Tick marks are annotated on the plots to coincide with the minimum and maximum points that bound the linear range. The derivative (i.e., slope) of the output/input curve was taken to ascertain linearity. For this analysis, slope values within the range of 0.8 to 1.2 are considered to be effectively linear for the purpose of measuring the dynamic range. FIGS. 17A & 17B show that backscatter communications can achieve 50-60 dB of linear range. FIG. 17B is the detail section 140 of the plot shown in FIG. 17A. The patch type tag is linear from about 30 μV up to 30 mV of input drive, while the dipole type tag is linear from about 100 μV up to 50 mV.

FIG. 16 shows overlays of the MsS modulation signal (input) applied to the patch-type tag and the recovered MsS signal (output) via the backscatter link. The plots clearly show that the output signal tracks the modulation input very closely. Although plots are not shown, similar results were obtained with the MsS modulation signal applied to the dipole-type tag.

Based on these results, it is seen that a simple backscatter tag consisting of only one active element and a printed antenna can be used to communicate an analog information signal with 50-60 dB of linear dynamic range. From a qualitative perspective, this level of fidelity appears to be quite adequate for a typical MsS echo return signal. The corresponding drive signal required to modulate the backscatter tag in its linear operating range is on the order of 10's of μVs up to 10's of mV.

Although the present invention has been described in terms of the foregoing preferred embodiments, this description has been provided by way of explanation only, and is not intended to be construed as a limitation of the invention. Those skilled in the art will recognize modifications of the present invention that might accommodate specific environments. Such modifications as to size, and even configuration, where such modifications are merely coincidental, do not necessarily depart from the spirit and scope of the invention.

We claim:
1. A thin-film magnetostrictive sensor (MsS), operable to generate and sense ultrasonic (high-frequency) mechanical waves travelling to and reflected from a flaw at a distance within a material, the MsS comprising:
    a multi-layer stack comprising a plurality of thin-film elements, each of the elements comprising:
        a soft magnetization layer; and
        a hard magnetization layer;
    an electrical insulation layer positioned on at least one face of the multi-layer stack of thin-film elements; and
    an electrically conductive planar coil positioned on a face of the electrical insulation layer opposite the multi-layer stack, the windings of the planar coil oriented in a plane adjacent and generally parallel to the face of the electrical insulation layer;
    wherein the coil generates a varying magnetic flux within a region around the coil as a result of the application of a varying electrical activation signal to the windings of the coil, thereby generating an outward bound mechanical wave into the material, the coil further generating an output electrical signal in the windings in response to a varying magnetic flux within the region around the coil as a result of the passage of an inward bound mechanical wave within the multi-layer stack adjacent the coil, the inward bound mechanical wave reflected from a flaw in the material.

2. The sensor of claim 1 wherein the soft magnetization layer comprises a crystalline iron cobalt layer.

3. The sensor of claim 1 wherein the hard magnetization layer comprises an amorphous iron terbium layer.

4. The sensor of claim 1 wherein the electrical insulation layer comprises an aluminum oxide layer.

5. The sensor of claim 1 wherein the soft magnetization layer of each of the plurality of thin-film elements, comprises a thickness in the range of 3-15 nm.

6. The sensor of claim 1 wherein the hard magnetization layer of each of the plurality of thin-film elements, comprises a thickness in the range of 3-15 nm.

7. The sensor of claim 1 wherein the soft magnetization layer and the hard magnetization layer in each of the plurality of thin-film elements each comprise a thickness of approximately 10 nm.

8. The sensor of claim 1 wherein the plurality of thin-film elements in the multi-layer stack comprises a quantity of thin-film elements in the range of 300-340 elements.

9. A method for manufacturing a monolithically integrated, multi-layered, thin-film sensor for flaw detection and monitoring, the sensor comprising a thin-film, multi-layer magnetostrictive stack, a thin-film electrically insulating layer, and a thin-film activating layer, the method comprising the steps of:
    magnetron sputtering of alternating layers of a high (hard) magnetostrictive material and a high magnetization (soft) material directly onto a sensing platform, the properties of the composite magnetostrictive layer engineered by adjusting layer thickness, soft/hard layer ratio and sputtering deposition parameters;
    post-annealing the composite magnetostrictive layers in a magnetic bias field;
    depositing a dielectric layer over top of the composite magnetostrictive layer using reactive magnetron sputtering, the dielectric layer to serve as an electrically insulating layer and for resistance to high temperature oxidizing environments; and
    depositing an activation layer, the activation layer comprising a conductive planar antenna coil, by means of shadow mask directly on top of the dielectric layer, wherein the sensor comprises the thin-film magnetostrictive sensor of claim 1.

10. The method of claim 9 wherein the surface of the sensing platform is treated chemically, thermally, or mechanically, or coated with an adhesion promoter layer to optimize impedance and mechanical adhesion of composite magnetostrictive film at elevated temperatures.

11. The method of claim 9 wherein a magnetic spin orientation is engineered as part of the manufacturing process thereby eliminating the need for magnetic biasing with permanent magnets prior to activation, or during operation.

12. The method of claim 9 wherein the dielectric layer and activation layer are deposited by methods selected from the group consisting of PVD, wet chemical, or plasma/flame spray techniques.

13. A method for monitoring the structural integrity of a moving component comprising the steps of:
- providing a thin-film, multi-layer magnetostrictive sensor according to claim 1 on the moving component;
- providing a receiver antenna on a non-moving component adjacent the moving component;
- implementing wireless communication to transmit the data acquired by the thin film multilayer sensor to the receiver antenna near or within the component under interrogation;
- implementing an RF backscatter modulator circuit with high fidelity for communicating analog response signals from the magnetostrictive sensor; and
- coupling RF signals from the antenna on the stationary component to an RF backscatter modulator on the rotating component.

* * * * *

UNITED STATES PATENT AND TRADEMARK OFFICE
CERTIFICATE OF CORRECTION

| | | |
|---|---|---|
| PATENT NO. | : 8,486,545 B2 | Page 1 of 1 |
| APPLICATION NO. | : 11/540495 | |
| DATED | : July 16, 2013 | |
| INVENTOR(S) | : Lanning et al. | |

It is certified that error appears in the above-identified patent and that said Letters Patent is hereby corrected as shown below:

In the Specification

Column 1, Line 19, insert:

--GOVERNMENT RIGHTS: The U.S. Government has a paid-up license in this invention and the right in limited circumstances to require the patent owner to license others on reasonable terms as provided for by the terms of Contract No. HR0011-04-C-0004 awarded by Defense Advanced Research Projects Agency (DARPA).--

Signed and Sealed this
Twelfth Day of November, 2013

Teresa Stanek Rea
*Deputy Director of the United States Patent and Trademark Office*